United States Patent
Shimada

(10) Patent No.: US 7,618,410 B2
(45) Date of Patent: Nov. 17, 2009

(54) DEVICES AND METHODS FOR ACCESS THROUGH A TISSUE WALL

(75) Inventor: Jin Shimada, Grantsburg, WI (US)

(73) Assignee: Cardia Access, Inc., St. paul, MN (US)

( * ) Notice: Subject to any disclaimer, the term of this patent is extended or adjusted under 35 U.S.C. 154(b) by 699 days.

(21) Appl. No.: 11/238,390

(22) Filed: Sep. 29, 2005

(65) Prior Publication Data

US 2006/0074397 A1   Apr. 6, 2006

Related U.S. Application Data

(60) Provisional application No. 60/615,984, filed on Oct. 5, 2004.

(51) Int. Cl.
*A61M 31/00* (2006.01)

(52) U.S. Cl. ...................................... 604/508

(58) Field of Classification Search ............. 604/523, 604/96.01, 912, 915, 917, 101.01, 508; 606/151, 606/157, 158, 191, 192, 194, 195, 198, 200, 606/213
See application file for complete search history.

(56) References Cited

U.S. PATENT DOCUMENTS

| | | | |
|---|---|---|---|
| 3,874,388 A * | 4/1975 | King et al. ........... | 606/232 |
| 4,164,221 A | 8/1979 | Bentley et al. | |
| 4,349,021 A | 9/1982 | Raible | |
| 4,402,681 A | 9/1983 | Haas et al. | |
| 4,610,665 A | 9/1986 | Matsumoto et al. | |
| 4,895,565 A | 1/1990 | Hillstead | |
| 5,269,326 A | 12/1993 | Verrior | |
| 5,303,234 A | 4/1994 | Kon | |
| 5,634,937 A | 6/1997 | Mollenauer et al. | |
| 5,697,911 A | 12/1997 | Yarger | |
| 5,797,870 A | 8/1998 | March et al. | |

(Continued)

OTHER PUBLICATIONS

Verrier et al., "Transatrial Access to the Normal Pericardial Space A Novel Approach for Diagnostic Sampling, Pericardiocentesis, and Therapeutic Interventions", Circulation, pp. 2331-2333, 1998.

(Continued)

*Primary Examiner*—Manuel A Mendez
(74) *Attorney, Agent, or Firm*—Dicke, Billig & Czaja, PLLC

(57) ABSTRACT

A method of accessing the pericardial space comprises providing a primary catheter having an inflatable balloon, inserting the primary catheter into the vascular system, forwarding the primary catheter through the vascular system to an atrial appendage, inflating the balloon to engage the wall of the appendage sufficient to separate opposing wall portions of the appendage between the cardiac tissue and the pericardium. The inflated balloon increases the distance of the pericardium from the cardiac tissue to permit easier access into the pericardial space via the appendage. The inflated balloon further can be configured to create a seal of the balloon exterior surface relative to an inner wall of the appendage adjacent to an apex of the appendage. The balloon seal isolates a portion of the interior of the appendage adjacent the apex allowing the removal of blood from the isolated portion. This prevents cross-contamination of fluid between the pericardial space and the appendage. An implantable valve positionable in the apex of the appendage permits repeatable access into the pericardial space.

7 Claims, 14 Drawing Sheets

U.S. PATENT DOCUMENTS

| | | | |
|---|---|---|---|
| 5,827,216 | A | 10/1998 | Igo et al. |
| 5,865,791 | A | 2/1999 | Whayne et al. |
| 5,931,810 | A | 8/1999 | Grabek |
| 5,968,010 | A | 10/1999 | Waxman et al. |
| 5,972,013 | A | 10/1999 | Schmidt |
| 6,156,009 | A | 12/2000 | Grabek |
| 6,162,195 | A | 12/2000 | Igo et al. |
| 6,200,303 | B1 | 3/2001 | Verrior et al. |
| 6,206,004 | B1 | 3/2001 | Schmidt et al. |
| 6,224,584 | B1 | 5/2001 | March et al. |
| 6,231,518 | B1 | 5/2001 | Grabek et al. |
| 6,237,605 | B1 | 5/2001 | Vaska et al. |
| 6,241,667 | B1 | 6/2001 | Vetter et al. |
| 6,266,550 | B1 | 7/2001 | Selmon et al. |
| 6,314,962 | B1 | 11/2001 | Vaska et al. |
| 6,314,963 | B1 | 11/2001 | Vaska et al. |
| 6,423,051 | B1 | 7/2002 | Kaplan et al. |
| 6,488,689 | B1 | 12/2002 | Kaplan et al. |
| 6,592,544 | B1 | 7/2003 | Mooney et al. |
| 6,592,552 | B1 | 7/2003 | Schmidt |
| 6,613,062 | B1 | 9/2003 | Leckrone et al. |
| 6,666,844 | B1 | 12/2003 | Igo et al. |
| 6,666,861 | B1 | 12/2003 | Grabek |
| 6,692,458 | B2 | 2/2004 | Forman et al. |
| 6,723,073 | B2 | 4/2004 | Ley et al. |
| 7,169,164 | B2 * | 1/2007 | Borillo et al. ............... 606/200 |
| 2003/0093194 | A1 | 5/2003 | Li et al. |

OTHER PUBLICATIONS

Pulerwitz et al., "Transatrial Access to the Normal Pericardial Space for Local Cardiac Therapy: Preclinical Safety Testing with Aspirin and Pulmonary Artery Hypertension", Journal of Interventional Cardiology, vol. 14, No. 5, pp. 493-498, 2001.

Gleason et al., "Myocardial Drug Distribution Pattern Following Intrapericardial Delivery: An MRI Analysis", Journal of Cardiovascular Magnetic Resonance, 4(3), pp. 311-316, 2002.

Sosa et al., "Gaining Access to the Pericardial Space", The American Journal of Cardiology, vol. 90, pp. 203-204, 2002.

* cited by examiner

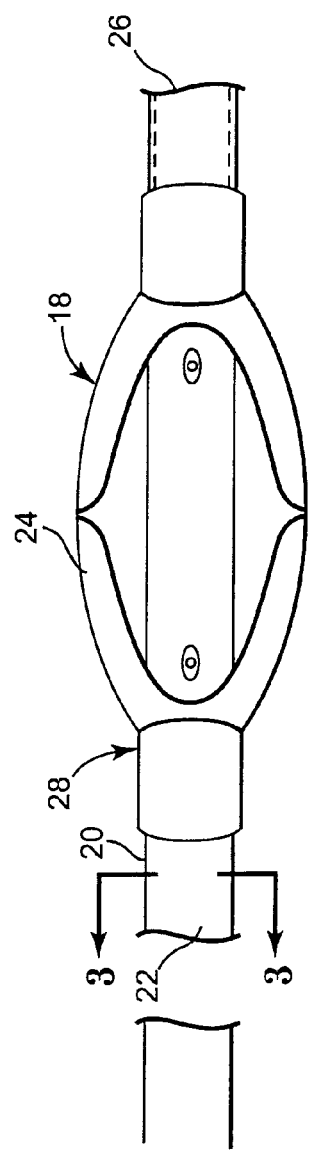
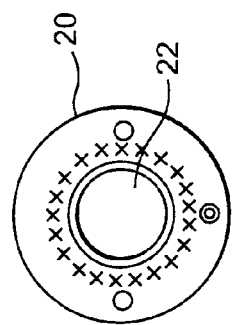
Fig. 2
Fig. 3

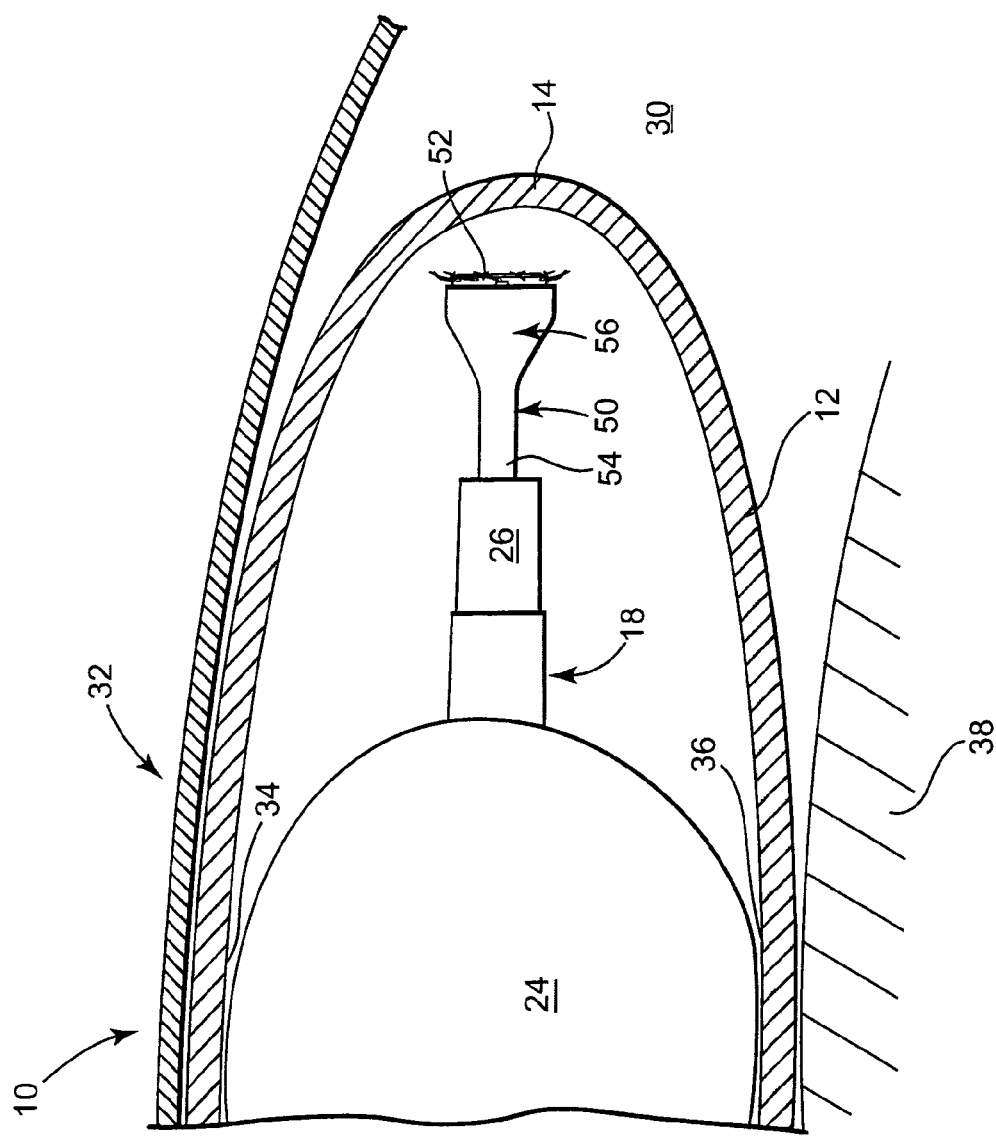

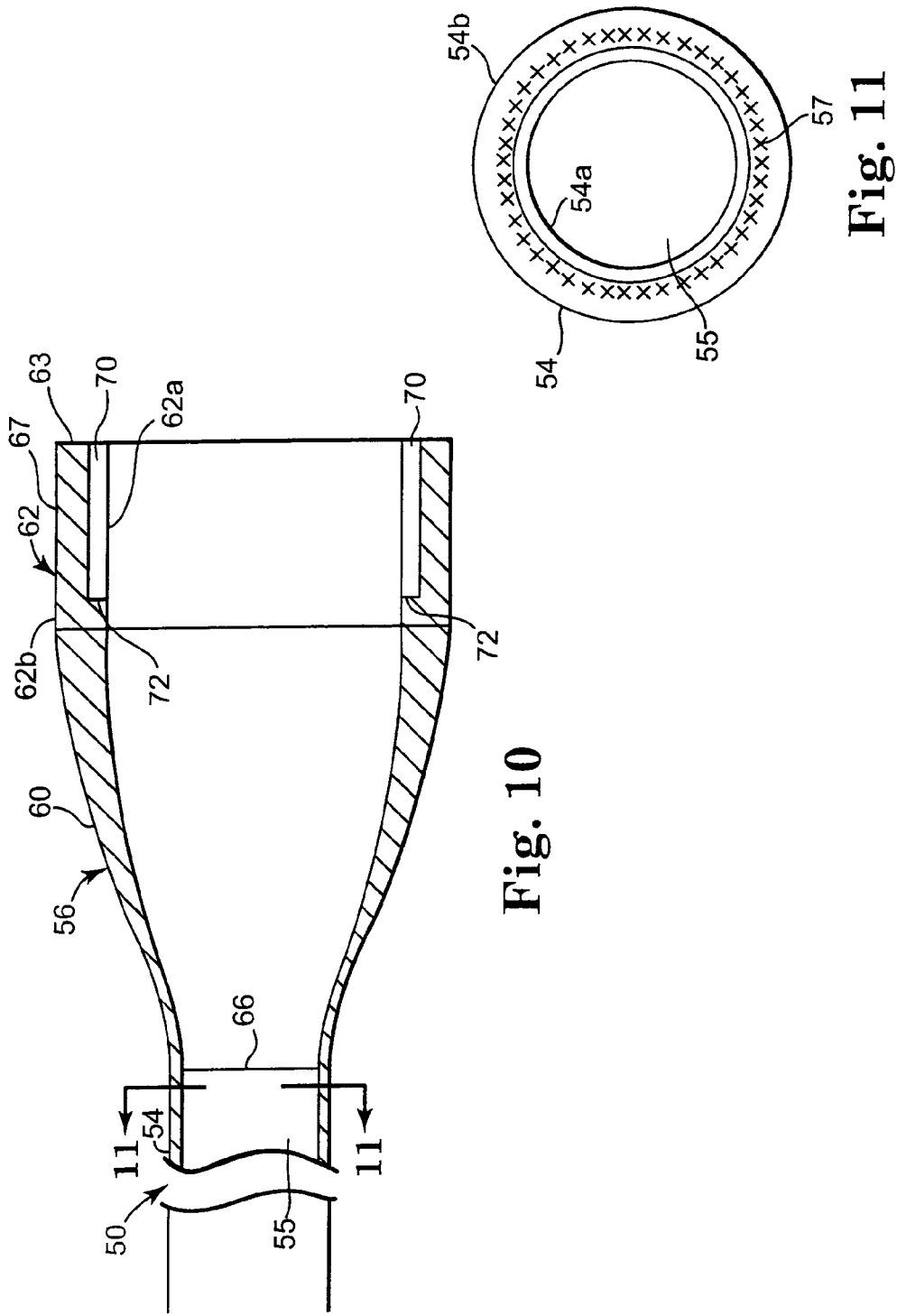

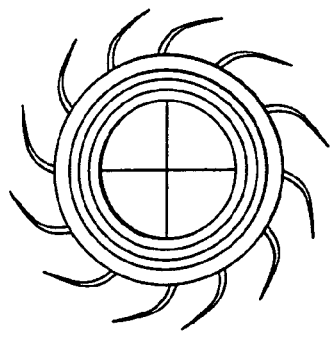
Fig. 13d
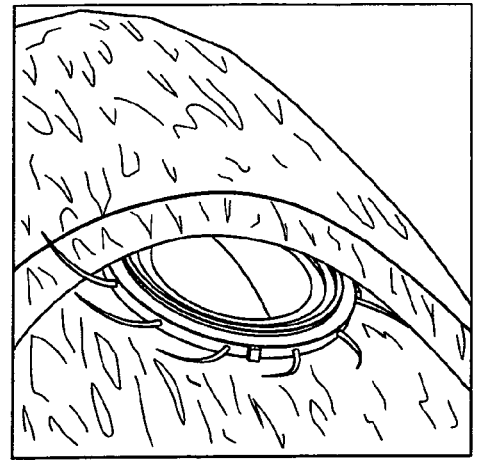
Fig. 13g
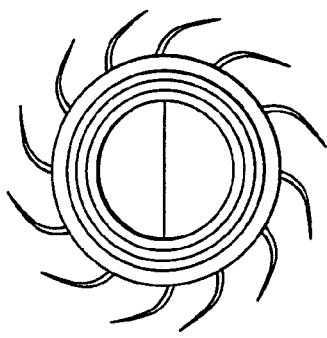
Fig. 13c
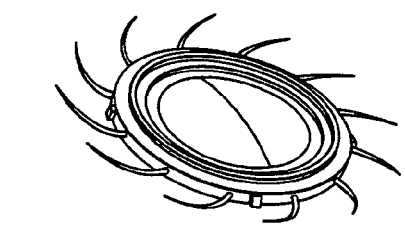
Fig. 13f
Fig. 13b
Fig. 13e

DEVICES AND METHODS FOR ACCESS THROUGH A TISSUE WALL

CROSS-REFERENCE TO RELATED APPLICATION

This application claims the benefit of Provisional Application No. 60/615,984 filed on Oct. 5, 2004 for "DEVICES AND METHOD FOR INITIAL AND/OR REPEATED ACCESS THROUGH TISSUE WALL".

BACKGROUND OF THE INVENTION

The present invention relates to a method and apparatus for accessing the pericardial space. More particularly, the present invention is directed to a method and apparatus for accessing the pericardial space via the right atrial appendage.

The pericardium is a membrane that surrounds the heart and isolates the heart from the remainder of the body. The small space between the heart and the pericardium is the pericardial space, which is filled with a fluid. The pericardial space has become an optimal location to administer cardiac treatments because the pericardial fluid is in constant contact with the heart muscle. However, the pericardial space is a confined area that is difficult to access without damaging the underlying heart tissue.

The right atrial appendage has become an ideal site for accessing the pericardial space because it is a thin-walled lobe that can easily be penetrated with a catheter. Also, the funnel-shape of the right atrial appendage acts as a guide for placing a catheter next to the apex of the appendage, which is adjacent to the pericardial space However, the apex of the right atrial appendage is in close proximity to the pericardial sack and the right atrium wall permitting little room for error when performing work on the right atrial appendage wall at the apex. This small amount of space creates a risk of puncturing the right atrium wall or pericardial sack with the catheter. In addition, there is a risk of mixing pericardial fluid from the pericardial space with blood in the right atrial appendage when the apex is pierced.

Therefore, there is a need in the art for a method and apparatus for accessing the pericardial space that reduces the risk of puncturing tissue not intended to be punctured and reduces the risk of mixing fluids.

BRIEF SUMMARY OF THE INVENTION

The invention is a method for accessing the pericardial space for performing a cardiac treatment. A primary catheter having an elongated body, an inflatable balloon attached at a distal end of the elongated body and a distal tip is inserted into the vascular system. The primary catheter is forwarded through the vascular system to position the distal end within an atrial appendage so that the distal tip is spaced adjacent to an apex of the appendage. The inflatable balloon is then inflated to create a seal of the balloon exterior surface relative to an inner wall of the appendage. Fluid from a segregated interior space of the appendage distal of the balloon seal is then evacuated.

BRIEF DESCRIPTION OF THE DRAWINGS

FIG. 2 is a side view of an end portion of a steerable balloon catheter used with the present invention.

FIG. 3 is a cross-sectional view of the balloon catheter of FIG. 2 taken along line 3-3.

FIG. 9 is a side view of an alternate embodiment of a working catheter of the present invention positioned within the inflated balloon catheter of FIG. 6.

FIG. 10 is a partial longitudinal sectional view of the working catheter of FIG. 9.

FIG. 11 is a cross-sectional view of the working catheter of FIG. 10 taken along line 11-11.

FIGS. 13a-13g are perspective views of an implantable device used with the working catheter of FIG. 9.

DETAILED DESCRIPTION

Figure 1:
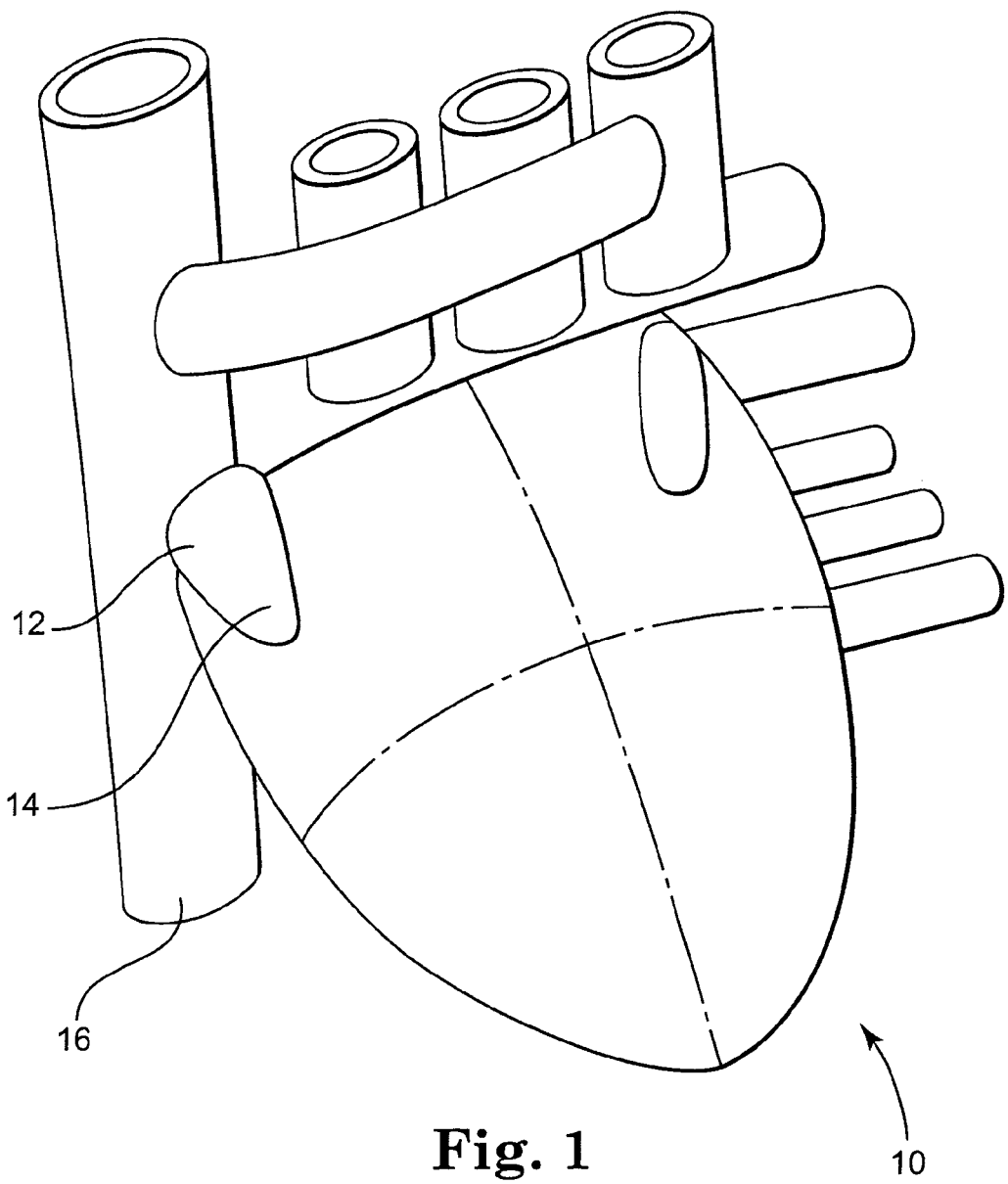
FIG. 1 is a diagrammatic view of a human heart.

The present invention is a method and apparatus for accessing the pericardial space via the right atrial appendage. FIG. 1 is a diagrammatic view of a human heart 10. The right atrial appendage 12 is a thin-walled, low pressure, ear-like lobe that can be readily accessed via the inferior vena cava 16 by way of the femoral vein (not shown). The right atrial appendage 12 is shaped such that it forms an apex 14 at one of its ends. The right atrial appendage 12 is a known entry site into the pericardial space (not shown) for the treatment of a variety of cardiac conditions.

FIGS. 2 and 3 are, respectively, side and cross-sectional views of an end portion of a steerable balloon catheter 18 known in the art for introducing and guiding a working catheter through the coronary vasculature. The balloon catheter 18 includes an elongated body 20, a central lumen 22 extending along the body 20, an inflation lumen extending along the body 20, an inflatable balloon 24, and a distal tip 26. The inflatable balloon 24 is attached to a distal end portion 28 of the body 20. The central lumen 22 is exposed at the distal tip 26 of the catheter 18 to permit a secondary, working catheter to be inserted through the central lumen 22 of the catheter 18 and to exit the distal tip 26. As illustrated in FIG. 3, the catheter 18 has a relatively large central lumen 22 that allows a secondary, working catheter to be advanced through the catheter 18 in order to perform a cardiac treatment such as drug delivery of heart growth factors, gene factors, cardio active agents and vessel active agents or diagnostic procedures such as use of a catheter based electrogram, use of catheter ablation of cardiac arrhythmias and cardiac pacing.

Figure 4:
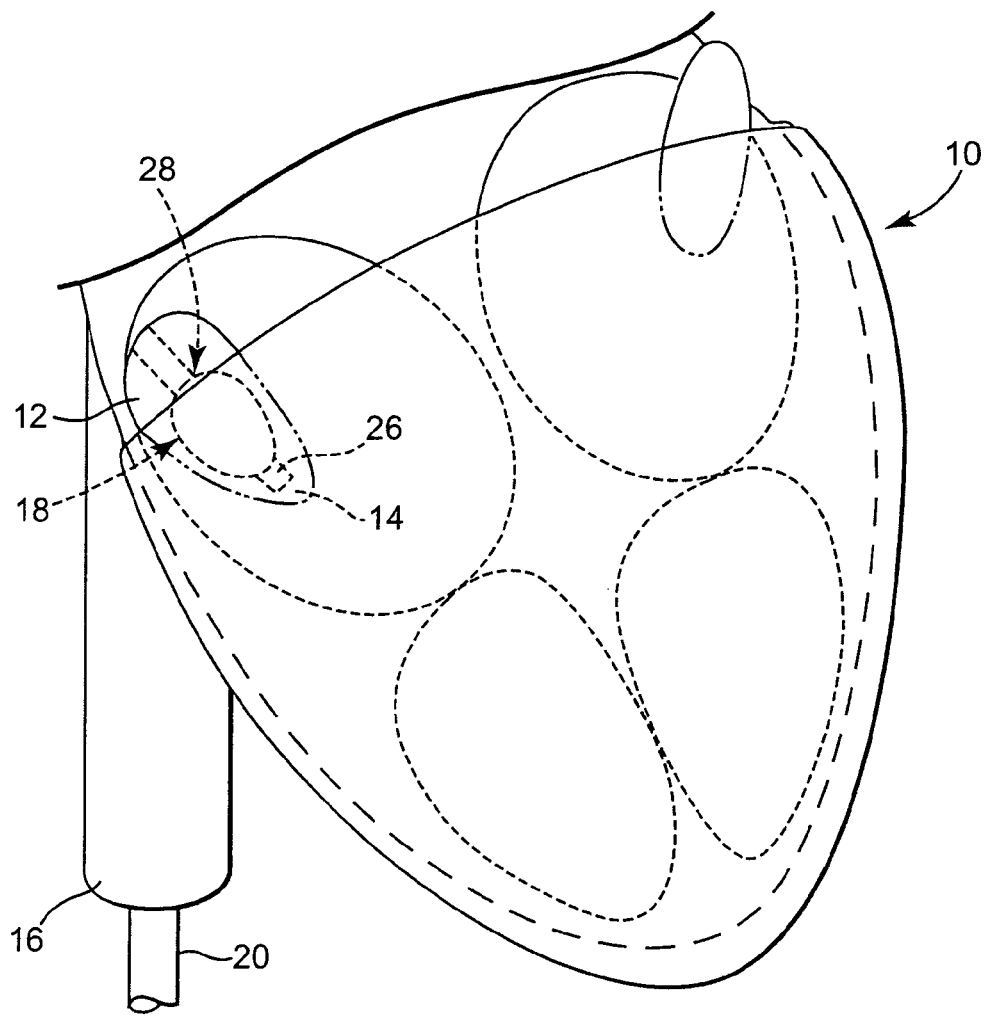
FIG. 4 is a diagrammatic view of a human heart partially enclosed by the pericardium.

FIG. 4 illustrates the distal tip 26 of balloon catheter 18 positioned in the right atrial appendage 12. Generally, the method of the present invention comprises advancing a balloon catheter 18 through the vascular system, such as via the femoral vein until the distal end portion 28 of the catheter 18 is within an atrial appendage, e.g., the right atrial appendage 12. The distal end portion 28 is guided far enough into the appendage so that the distal tip 26 is spaced from and proximate to the apex 14 of the appendage. The balloon 24 attached to the catheter 18 is then inflated in order to engage the inner wall surface of the appendage in a manner that will be discussed herein in greater detail.

Figure 5:
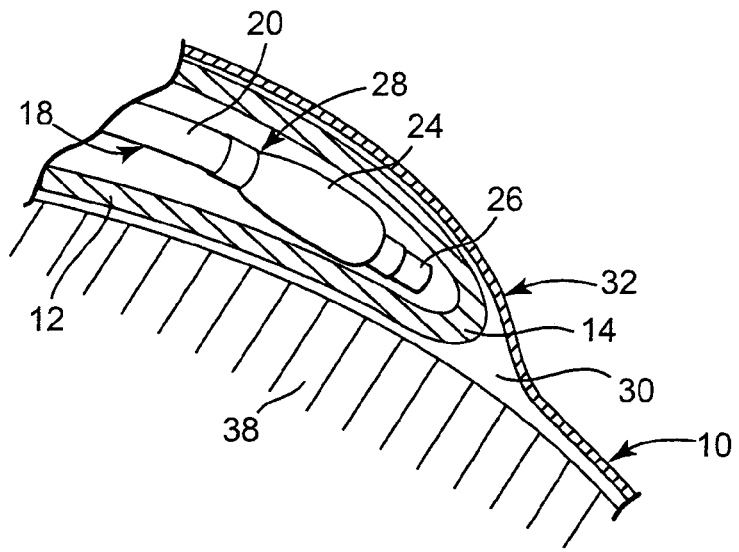
FIG. 5 is a cross-sectional view of the right atrial appendage with the balloon catheter of FIG. 3 in an uninflated state.

FIGS. 5-8 illustrate one embodiment of a method for accessing the pericardial space 30 via the right atrial appendage 12. Balloon catheter 18 is inserted into the vascular system via the femoral vein (not shown) and advanced to the right atrial appendage 12 with balloon 24 in a deflated state. The distal end portion 28 is positioned in the right atrial appendage 12 such that the distal tip 26 is spaced from and adjacent to the apex 14 of the right atrial appendage 12. This position aligns tip 26 with apex 14 and permits a working catheter to be advanced through the catheter 18 to perform a procedure on the appendage wall at the apex 14, such as a piercing procedure through the wall of the apex 14 to access the pericardial space 30. As seen in FIG. 5, near apex 14 the pericardium lining 32 is in close proximity to the right atrium wall 38. Access into the pericardial space 30 through the wall 38 of the right atrium with a piercing-type catheter, without puncturing the pericardium lining 32 or the right atrium wall 38, is thus difficult.

Method of Increasing the Pericardial Space Adjacent the Appendage Apex

Figure 6:
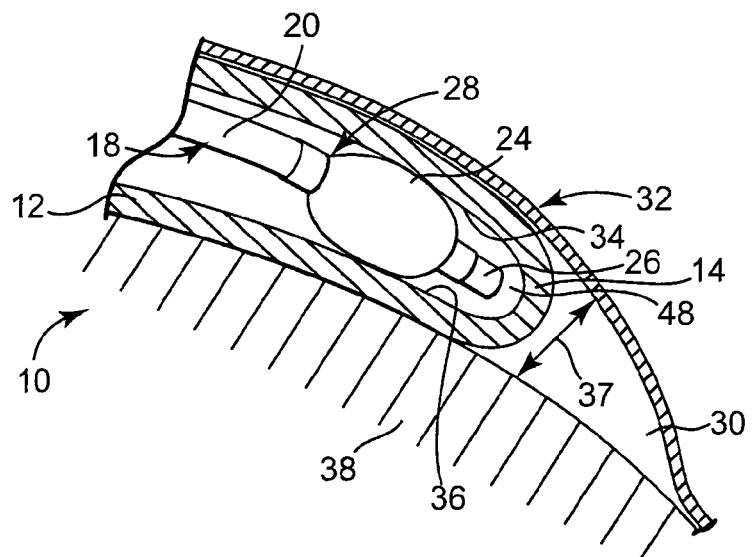
FIG. 6 is a cross-sectional view of the right atrial appendage with the balloon catheter of FIG. 3 in an inflated state.

As shown in FIG. 6, once distal end portion 28 of catheter 18 is positioned in the right atrial appendage 12, balloon 24 is inflated to engage the internal wall portions 34 and 36 of the right atrial appendage 12 causing opposing internal wall portions 34 and 36 of the appendage 12 to separate. As the internal wall portions 34 and 36 separate, the pericardial sack lining 32 becomes spaced farther apart from the right atrium wall 38. In one exemplary embodiment, balloon 24 is selected to have an inflated outer diameter substantially larger than the normal spacing of wall portions 34, 36 such that the pericardial space 30 as measured between wall portions 34 and 36 adjacent to the apex 14 (shown at line 37) is increased by at least approximately 1.5 to 2.0 millimeters. The increased pericardial space 30 decreases the probability of puncturing or piercing tissue with the working catheter that is not intended to be punctured or pierced such as the pericardial sack 32 or the right atrium wall 38. Additionally, the increased pericardial space 30 provides a larger working area within the pericardium to perform cardiac treatments with a working catheter.

Method of Sealing the Appendage Adjacent to the Apex

To further improve access to the pericardial space 30, in an alternate embodiment of the present invention, balloon 24 is selected to have a size and shape sufficient, when inflated, to create a fluid-tight seal between the exterior surface of balloon 24 relative to the inner wall of the right atrial appendage 12. As shown in FIG. 6, by inflating balloon 24 to create a seal relative to the appendage wall, a space 48 between the distal end of the balloon 24 and the apex 14 is isolated from the cardiovascular system, allowing the removal of blood in space 48 so as to prevent any cross-contamination between the cardiovascular system and the pericardial fluid when the pericardium is accessed with a piercing catheter.

Figure 7:
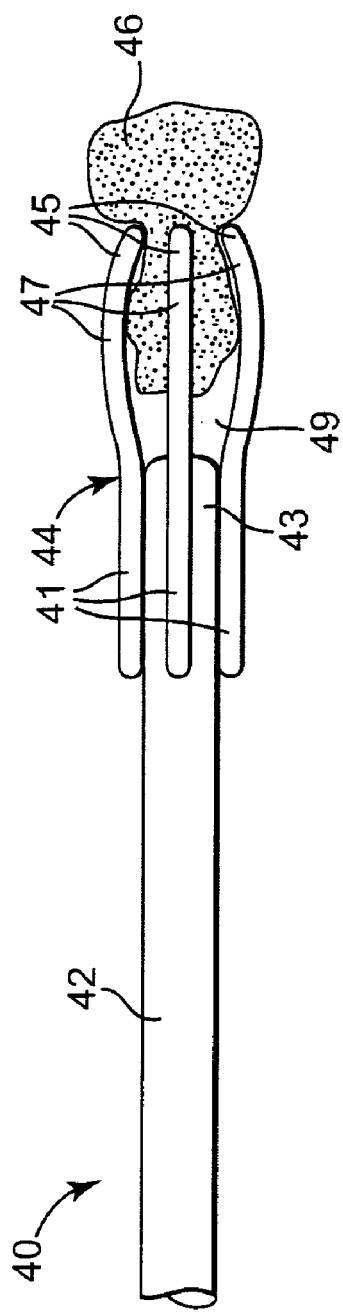
FIG. 7 is a partial side view of a working catheter of the present invention used with the balloon catheter of FIG. 3.

Apparatus and Method of Preventing Cross-Contamination of Fluids in Right Atrial Appendage FIG. 7 is a partial side view of one embodiment of an apparatus for removing blood from space 48. The apparatus comprises a working catheter 40 with an elongated body 42 having a working portion 44. The elongated body 42 has a length and outer diameter that allows body 42 to be inserted into the central lumen 22 of the primary balloon catheter 18, advanced through catheter 18 and out the distal tip 26. Body 42 may be made from a suitable bio-compatible polymer and may have one or more lumens that extend the length of body 42. In the embodiment shown, body 42 terminates at a distal end 43 that may be sealed or plugged, such as with a silicone material.

Working portion 44 is located adjacent to distal end 43 of catheter 40. Working portion 44 comprises a plurality of fingers 47 having a first portion 41 connected to the outer surface of distal end 43 of catheter 40 and a second portion 45 that extends from distal end 43. Fingers 47 maybe formed from a flexible material, such as bio-compatible metal, for example stainless steel, or a polymer such as polyethylene. Fingers 47 are radially spaced about body 42 near the distal end 43 and are secured to catheter 40 by welding or a bio-compatible adhesive. The second portion 45 of fingers 47 have a length and configuration that form a bulbous-shaped holding area 49 having an outer diameter greater than the outer diameter of catheter body 42. Positioned within the holding area 49 is an absorbent material 46, such as polyester or cotton. Fingers 47 have sufficient flexibility to spread apart to load a first portion of the absorbent material 46 in the holding area 49 with a second portion extending from fingers 47. Fingers 47 apply a holding force adequate to retain the first portion of the absorbent material 46 in the holding area 49. The fingers 47 are sized to fit into the central lumen 22 of the primary balloon catheter 18, advanced through catheter 18 and out the distal tip 26.

Figure 8:
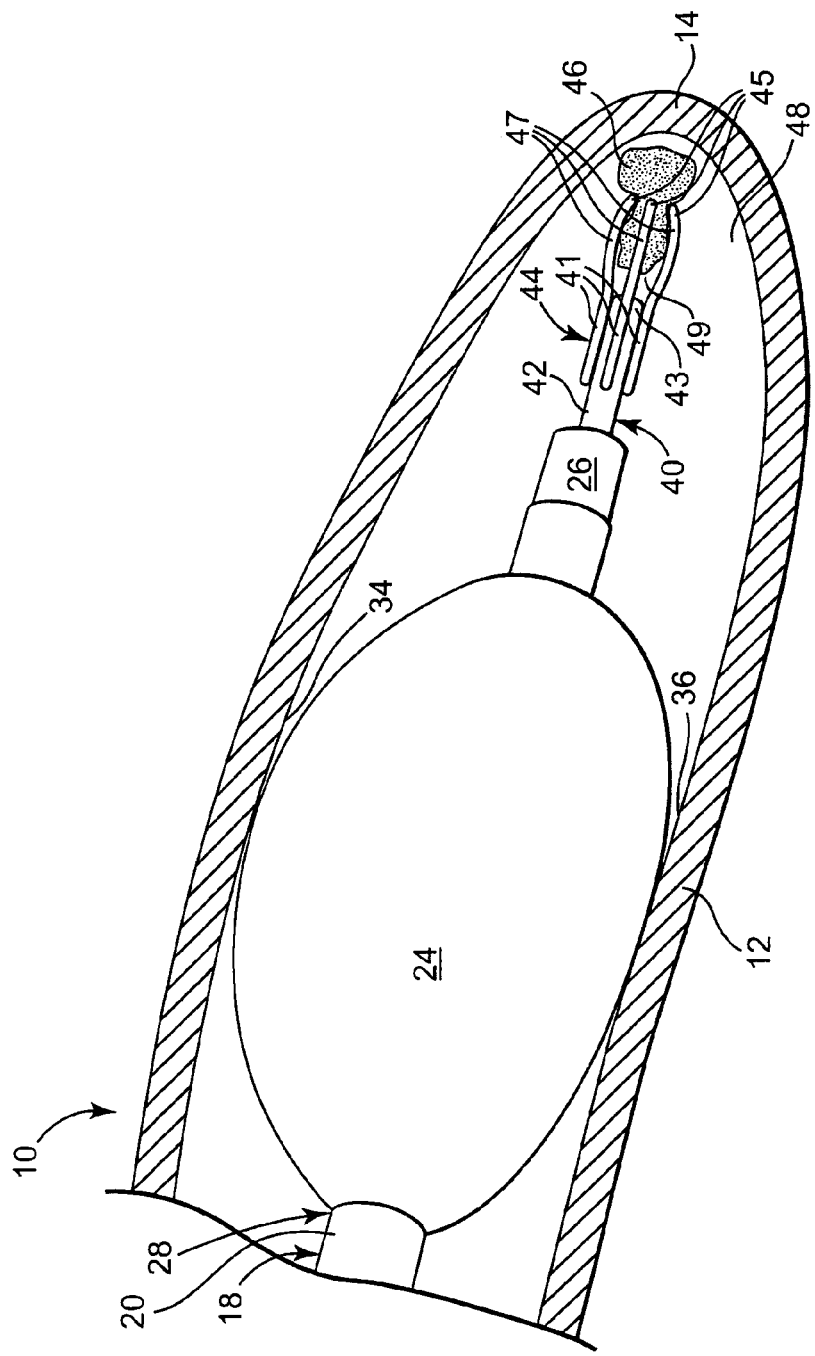
FIG. 8 is a side view of the working catheter of FIG. 7 positioned within the inflated balloon catheter of FIG. 6.

FIG. 8 illustrates an inflated balloon 24 of catheter 18 with the catheter 40 advanced through the primary catheter 18 and positioned within the right atrial appendage 12. As shown in FIG. 8, catheter 40 includes absorbent material 46 loaded within the holding space 49 of the catheter 40. Catheter 40 is inserted into the central lumen 22 of the primary balloon catheter 18 and advanced through the central lumen 22 until the working portion 44 exits the distal tip 26 of the primary catheter 18 thereby permitting the absorbent material 46 to absorb blood isolated within space 48. Catheter 40 is then withdrawn and the steps of inserting a catheter 40 loaded with an absorbent material 46 is repeated as necessary to remove all blood from space 48. Once all blood has been removed from space 48, the wall of apex 14 may be swabbed with additional absorbent material 46 loaded on catheter 40, as shown in FIG. 8. The removal of blood from space 48 prevents the mixing of blood and pericardial fluid of the pericardial space 30 when apex 14 is pierced with a piercing catheter. In addition, following a piercing of the wall of apex 14, catheter 40 may be loaded with absorbent material to which has been applied collagen for swabbing the pierced wall to aid in plugging the puncture site of the wall.

In an alternative embodiment, catheter 40 may comprise a dual lumen catheter having both lumens exposed at the distal end 43 of catheter 40. Blood in space 48 maybe removed by injecting a saline solution through the first lumen of the catheter into space 48 with a return flow of the flushed blood and saline solution through the second lumen.

Once space 48 has been cleared of all blood, a working catheter configured with a piercing tip maybe advanced through catheter 18 until the piercing tip is spaced from and adjacent to the apex 14. The position of catheter 18 aligns the piercing tip with the apex 14 for piercing through the apex 14 wall to access the pericardial space 30. The working catheter maybe any catheter known in the art that carries a piercing device such as drug injection catheters, lead wire placement catheters or mapping catheters.

Apparatus and Method of Implanting a Device in Right Atrial Appendage

FIG. 9 shows a side view of one embodiment of a catheter system 50 for use with the balloon catheter 18 of FIG. 6 for enabling repeated access into the pericardial space 30 through the wall of apex 14 with a piercing device. Generally, catheter system 50 comprises an elongated body 54 and a flared distal portion 56. Elongated body 54 has a length and outer diameter that allows body 54 to be inserted into the central lumen 22 of catheter 18 and advanced through catheter 18 to space 48. Body 54 maybe made from a suitable bio-compatible polymer or metal such as stainless steel.

Flared distal portion 56 has an outer diameter that is larger than body 54. Flared distal portion 56 is configured to hold an implantable device 52 in a manner to be described herein in greater detail.

FIG. 10 is a partial longitudinal sectional view of elongated body 54 and flared distal portion 56 of catheter system 50. As shown in FIG. 10, elongated body 54 has a central lumen 55 that allows a working catheter to be advanced through the catheter system 50 in order to perform a cardiac treatment. As shown in FIG. 11, elongate body 54 is comprised of inner cylindrical jacket 54a and outer cylindrical jacket 54b which are extruded from a bio-compatible polymer such as PEBAX, a thermoplastic elastomer resin by the ATOCHEM Corporation of France. Positioned between the inner and outer jackets 54a, 54b is a braided wire coil 57. Elongated body 54 may be constructed in the manner disclosed and taught in U.S. Pat. No. 6,582,536, which is incorporated herein by reference. In one embodiment, body 54 has an inner and outer diameter smaller than the flared distal portion 56 for increased flexibility of catheter 50. Alternatively, body 54 and distal portion 56 may have the same inner and outer diameter.

Referring again to FIG. 10, flared distal portion 56 comprises a conical portion 60 and a cylindrical portion 62 molded from a bio-compatible polymer such as PEBAX, a thermoplastic elastomer resin by the ATOCHEM Corporation of France. The molded flared distal portion 56 is bonded by heat to the elongated body 54 to form the catheter system 50. The flared distal portion 56 of catheter system 50 has a length of approximately 0.25 inches.

Conical portion 60 has a length that extends approximately half of the length of the flared distal portion 56. The conical portion 60 transitions the inner and outer diameter of catheter 50 to a size suitable for permitting distal portion 56 to carry an implantable device 52.

Cylindrical portion 62 has a length that extends approximately half of the length of the flared distal portion 56. Cylindrical portion 62 has an inner cylindrical surface 62a and an outer cylindrical surface 62b which defines a cylindrical wall 67 of cylindrical portion 62. Wall 67 has a greater wall thickness than the wall of body 54. Radially spaced about the inner surface 62a are a plurality of grooves 70. Grooves 70 extend longitudinally from distal end 63 of distal portion 56 for a substantial length of cylindrical portion 62. A shoulder 72 defines the end of grooves 70.

Figure 12:
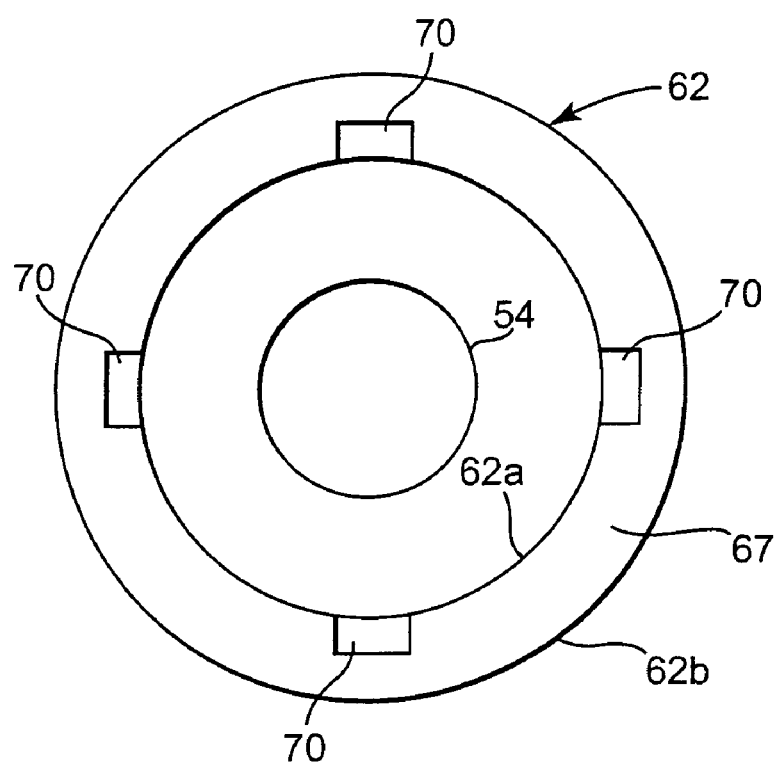
FIG. 12 is an end view of the working catheter of FIG. 10.

FIG. 12 is an end view of the cylindrical portion 62 of the flared distal portion 56. In one embodiment, cylindrical portion 62 includes four grooves 70 which in one embodiment have a depth of about half of the wall thickness of wall 67. As viewed in FIG. 12, in the embodiment shown grooves 70 are configured to have a rectangular shape. Although the cylindrical portion 62 shown in FIG. 12 has four grooves 70, cylindrical portion 62 can have two or more grooves 70. In a preferred embodiment, grooves 70 are equally radially spaced about the inner wall surface 62a of the cylindrical portion 62.

Figure 13A:
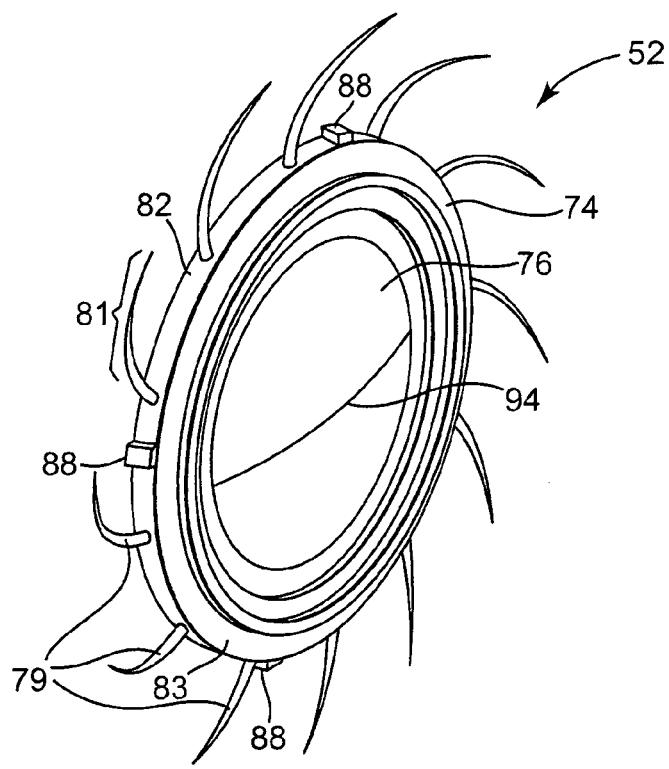

FIGS. 13a-13g are perspective views of a first embodiment of an implantable valve 52 used with the catheter system 50. As seen in FIG. 13a, generally, implantable valve 52 comprises a cylindrical frame 74 and a seal 76. Seal 76 is positioned within an opening of cylindrical frame 74. Cylindrical frame 74 is molded from a rigid material such as a bio-compatible metal, for example, nitinol, or stainless steel, or expandable mesh or a rigid polymer such as polyethylene. Extending radially outward from outer circumferential surface 82 of cylindrical frame 74 are a plurality of radially spaced ribs 88. Ribs 88 are configured to mate with grooves 70 of cylindrical portion 62 of catheter 50 so that the valve 52 can be carried by the catheter system 50. In one embodiment, ribs 88 have a length that extends substantially the width of outer circumferential surface 82 of cylindrical frame 74.

Also, extending radially outward from the outer circumferential surface 82 of cylindrical frame 74 are a plurality of fixation elements 79. One end of each fixation element 79 is molded to the outer circumferential surface 82 of cylindrical frame 74. Each fixation element 79 extends radially from outer circumferential surface 82 and in the embodiment shown is configured to curve generally in a clockwise direction. End portion 81 of each fixation element 79 also is configured to curve in an axial direction. End portion 81 of each fixation element 79 has an acicular and/or barbed terminus. In an alternate embodiment, fixation elements 79 may be configured to have a helical configuration or to include a ribbed tip. Fixation elements 79 are made of a bio-compatible metal such as stainless steel or nitinol or a rigid polymer such as polyethylene. Although twelve fixation elements 79 are depicted, the valve 52 can have two or more elements 79. In a preferred embodiment, the fixation elements 79 are equally radially spaced about outer circumferential surface 82. The outer end surface 83 of cylindrical frame 74 may include a layer of a sealable, compliant bio-compatible material such as silicone.

Seal 76 is a molded layer of a soft, resilient bio-compatible material such as silicone. Seal 76 is configured to have a concave/convex configuration and an outer diameter approximately equal to the diameter of the opening of cylindrical frame 74. In one embodiment, seal 76 includes a slit 94 that extends substantially along a diameter of seal 76.

Figure 14:
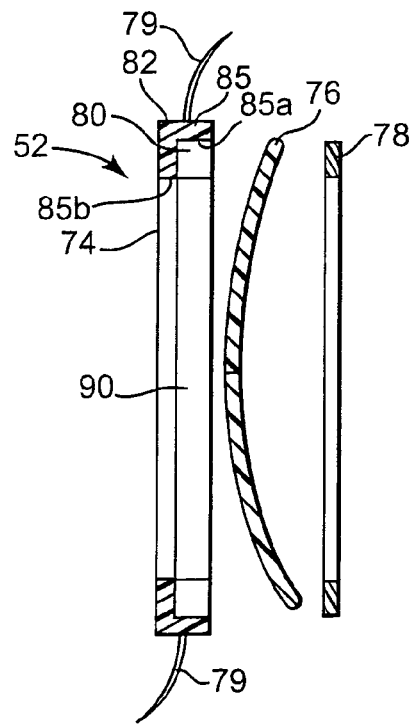
FIG. 14 is a cross-sectional exploded view of the implantable device of FIGS. 13a-13g.

FIG. 14 is an exploded cross-sectional view of the implantable valve 52. Cylindrical frame 74 comprises a stepped inner cylindrical surface 85 which forms inner cylindrical surface portions 85a and 85b. Portion 85b has a smaller diameter than portion 85a and defines an opening 90 of valve 52. Between portions 85a, 85b is a radial shoulder 80. Portion 85a has an outer diameter sized to receive seal 76. As further shown in FIG. 14, each fixation element 79 extends beyond an end surface of frame 74 for implanting valve 52 in tissue as will be described herein in greater detail.

Seal 76 is positioned within portion 85a of cylindrical frame 74 until it contacts shoulder 80. A retaining ring 78 having an outer diameter approximating the inner diameter of portion 85a is then positioned within portion 85a to secure a seal between shoulder 80 and retaining ring 78. Retaining ring 78 is bonded to cylindrical frame 74 by heat or an adhesive.

Retaining ring 78 is molded from a rigid material such as a bio-compatible metal, for example, nitinol, stainless steel, and expendable mesh or a rigid polymer such as polyethylene.

Figure 15:
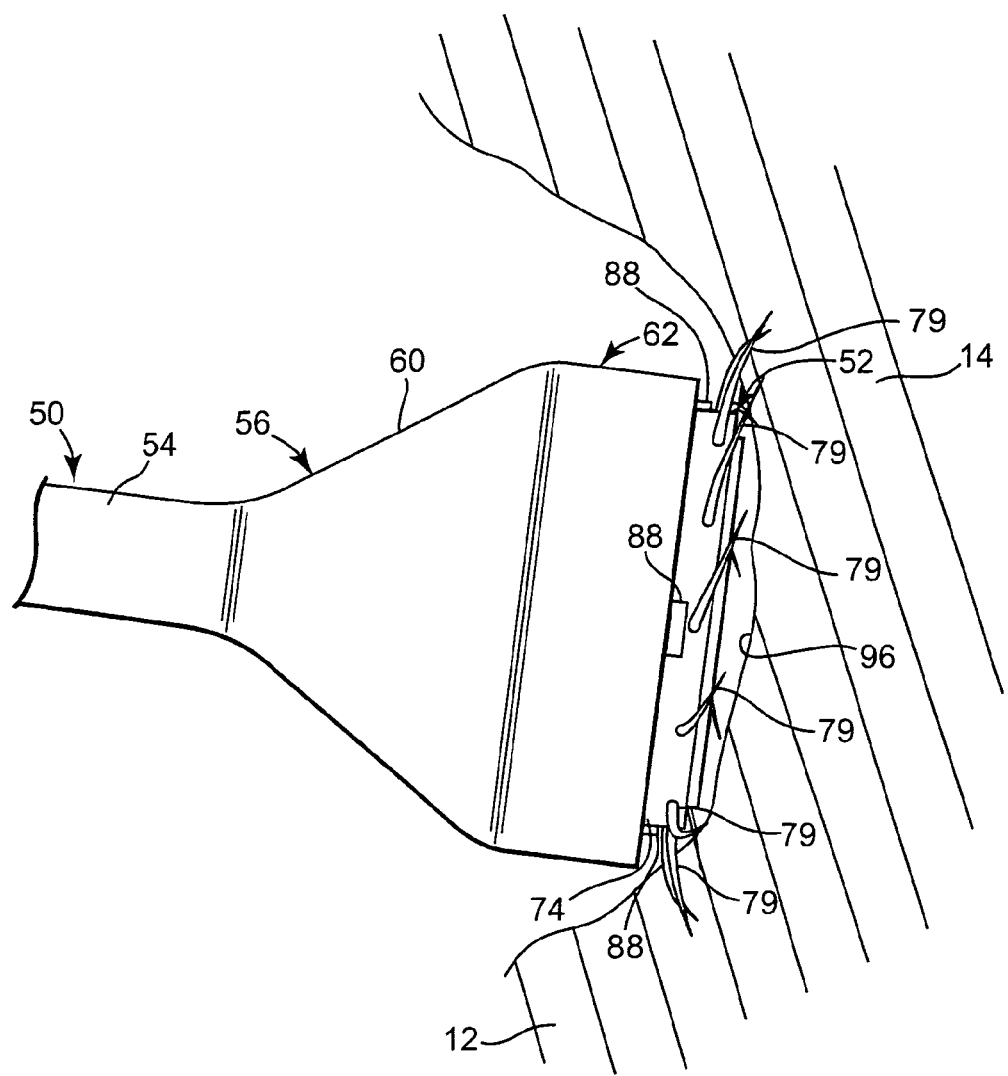
FIG. 15 is a diagrammatic view of the implantable device carried by the working catheter of FIG. 9 during implantation.

FIG. 15 is a diagrammatic view of valve 52 carried by catheter system 50 positioned within the right atrial appendage 12. Valve 52 is connected to cylindrical portion 62 of the catheter system 50 with ribs 88 on the cylindrical frame 74 of the valve 52 engaging grooves 70 on the cylindrical portion 62. Grooves 70 and ribs 88 are sized to securely hold valve 52 to the catheter system 50 for delivery to the right atrial appendage 12. Valve 52 is positioned within the cylindrical portion 62 until cylindrical frame 74 contacts shoulders 72 of grooves 70.

Once valve 52 is secured to the catheter system 50, the catheter system 50 is guided by the primary catheter 18 to the apex 14. Valve 52 is implanted by advancing catheter system 50 forward until fixation elements 79 of valve 52 contact inside wall 96 of the apex 14. In the embodiment shown, catheter system 50 is then axially rotated causing fixation elements 79 of valve 52 to penetrate the tissue of the apex 14 and draw valve 52 into wall 96.

Figure 16:
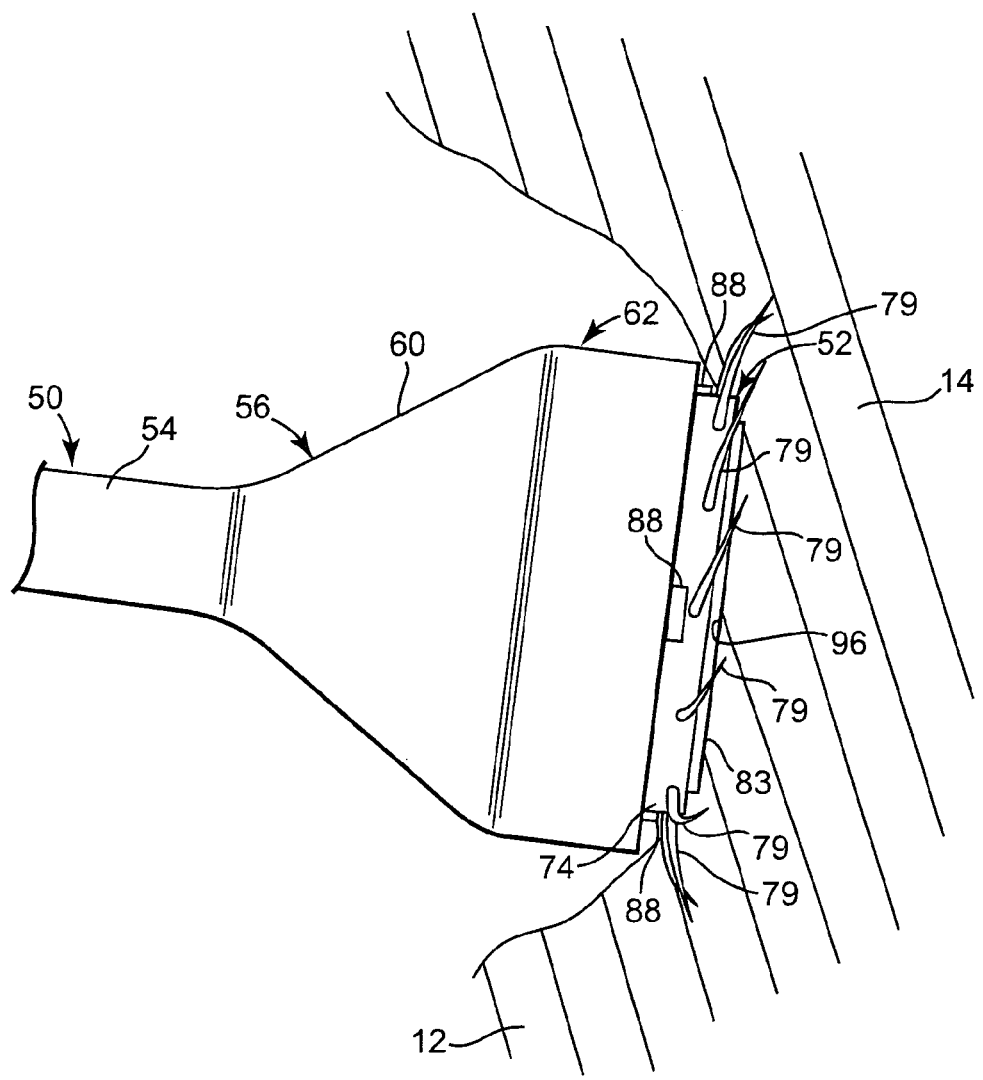
FIG. 16 is a diagrammatic view of the working catheter of FIG. 9 with the implantable device implanted.

FIG. 16 is a diagrammatic view of catheter system 50 with valve 52 implanted into wall 96 of apex 14. As the fixation elements 79 grasp deeper into wall 96 of apex 14, the outer end surface 83 of valve 52 is drawn against wall 96 to create a seal between the outer end surface 83 of cylindrical frame 74 and wall 96. A working catheter known in the art having a distal end configured to pierce through wall 96 can then be inserted and advanced through the catheter system 50 and pierced through valve seal 76 and wall 96 of apex 14 to access the pericardial space 30 without a mixing of fluids from the vascular system and the pericardial sac.

The distal end of the piercing catheter can then perform a cardiac treatment in the pericardial space 30. When the cardiac treatment is completed, the piercing catheter is withdrawn from catheter system 50. Catheter system 50 and the primary balloon catheter 18 can then either be removed from the vascular system, or another cardiac treatment can be performed bypassing another working catheter through catheter system 50 and valve 52. Catheters 18 and 50 can be removed with valve 52 remaining anchored to the apex 14 tissue permitting future access to the pericardial space 30 such as via a balloon catheter 18 and/or a balloon catheter 18 in combination with catheter 50. Implanted valve 52 allows repeated access to the pericardial space 30 while preventing mixing of the pericardial fluid and fluid from the vascular system.

To remove valve 52 from wall 96 of apex 14, the primary balloon catheter 18 is guided to the right atrial appendage 12. Catheter system 50 is advanced through the primary balloon catheter 18 and flared distal portion 56 is guided to align and engage grooves 70 on the cylindrical portion 62 with ribs 88 on the cylindrical frame 74. The catheter system 50 is then axially rotated in an opposite direction causing fixation elements 79 to be extracted from the wall 96 of apex 14. The catheter system 50 with the implantable valve 52 is then removed from the vascular system.

Figure 17:
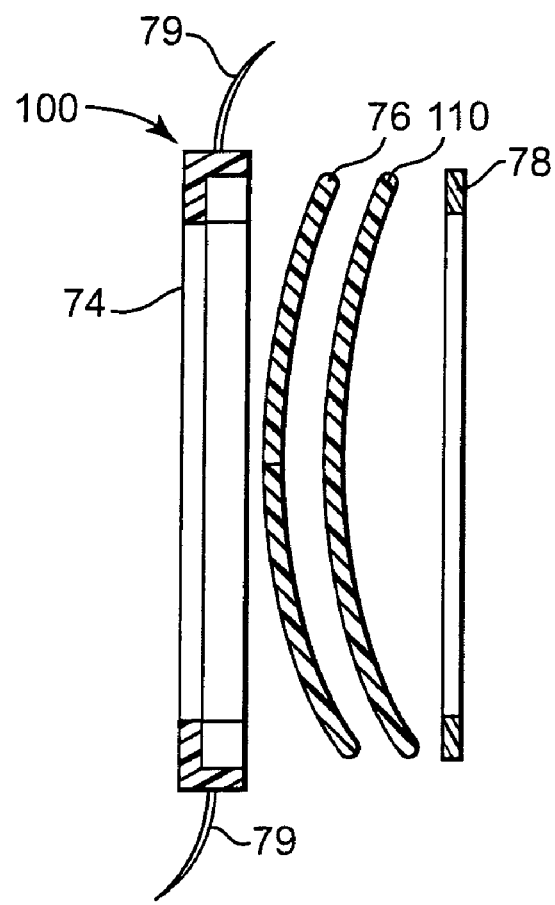
FIG. 17 is a cross-sectional exploded view of an alternate embodiment of an implantable device.

FIG. 17 illustrates a cross-sectional, exploded view of an alternate embodiment of an implantable valve 100. Valve 100 is configured substantially similar to valve 52 with respect to frame 74, seal 76 and retaining ring 78, with the only difference being the addition of a second seal 110 adjacent to seal 76. Second seal 110 is configured the same as seal 76 but is oriented relative to seal 76 with its slit at an angle relative to slit 94 of seal 76. Second seal 110 of valve 100 enhances the sealing performance of the valve 100.

The present invention teaches a method of using an inflatable balloon catheter within the right atrial appendage to increase the pericardial space in order to provide a large working area within the pericardium to perform cardiac treatments. The present invention also teaches a method of inflating a balloon within the right atrial appendage to create a fluid-tight seal between the exterior surface of the balloon relative to the inner wall of the right atrial appendage. The fluid-tight seal creates an isolated space adjacent to the apex of the right atrial appendage allowing for the removal of blood in the space to prevent any cross-contamination between the cardiovascular system and the pericardial fluid when the pericardium is accessed with a piercing catheter.

The present invention further teaches a working catheter for use with balloon catheter and a method of using the working catheter to remove blood from the isolated space adjacent to the apex of the right atrial appendage. Working catheter carries an absorbent material that is advanced into the isolated space of the right atrial appendage. The absorbent material absorbs blood within the space. The removal of blood prevents cross-contamination of fluid of the vascular system and fluid of the pericardial space during a cardiac treatment within the pericardial space.

Finally, the present invention teaches a second working catheter for use with balloon catheter for allowing repeated access into the pericardial space and a method of using the second working catheter. The second working catheter carries an implantable valve that is implanted within the wall of apex 14 of the right atrial appendage to permit repeated access to the pericardial space while preventing mixing of the pericardial fluid and fluid from the vascular system.

The implantable valve of the present invention comprises a cylindrical frame, a seal positioned within the frame and a retaining ring that secures the seal to the frame. The frame is configured to mate with an end portion of the second working catheter. Extending radially outward from an outer circumferential surface of the frame are a plurality of fixation elements which are configured to penetrate the tissue at the apex of the right atrial appendage and secure the valve to the wall of the apex. The valve permits a piercing-type working catheter to access the pericardial space and prevent mixing of fluids between the vascular system and the pericardial space. The valve may remain implanted in the tissue to permit repeated access into the pericardial space by one or more working catheters to perform a cardiac treatment. While the method of implanting a valve has been explained with reference to the wall of the apex of the right atrial appendage, the valve can be implanted in any wall tissue.

Although the present invention has been described with reference to preferred embodiments, workers skilled in the art will recognize that changes maybe made in form and detail without departing from the spirit and scope of the invention.

The invention claimed is:

1. A method for accessing a pericardial space comprising:
   providing a primary catheter having an elongated body, a central lumen extending along the body, an inflation lumen extending along the body and an inflatable balloon attached at a distal end portion of the body, such that an interior of the balloon communicates with the inflation lumen, the ballon having an exterior surface, the central lumen being exposed at a distal tip of the primary catheter;

inserting the primary catheter into the vascular system;

forwarding the primary catheter through the vascular system to position the distal end portion within an atrial appendage with the distal tip spaced from an apex of the atrial appendage;

inflating the balloon to create a seal of the balloon exterior surface relative to an inner wall of the atrial appendage; and evacuating blood from a segregated interior space of the atrial appendage distal of the balloon seal.

2. The method of claim 1 further comprising:

providing a secondary catheter having an elongated body with an outer diameter smaller than an inner diameter of the central lumen of the primary catheter;

inserting the secondary catheter into the central lumen of the primary catheter; and advancing the secondary catheter through the central lumen to the distal tip of the primary catheter.

3. The method of claim 1 further comprising:

providing a secondary catheter having a distal working portion for performing a treatment external to the primary catheter.

4. A method for accessing a pericardial space comprising:

providing a primary catheter having an elongated body, a central lumen extending along the body, an inflation lumen extending along the body and an inflatable balloon attached at a distal end portion of the body, such that an interior of the balloon communicates with the inflation lumen, the central lumen being exposed at a distal tip of the primary catheter;

inserting the primary catheter into the vascular system;

forwarding the primary catheter through the vascular system to position the distal end portion within an atrial appendage with the distal tip spaced from an apex of the atrial appendage; and inflating the balloon to engage an internal wall of the atrial appendage and separate opposing atrial appendage wall portions, whereby a pericardial sack in contact with an external wall of the atrial appendage and an atrial wall becomes spaced from the atrial wall.

5. The method of claim 4 further comprising:

inflating the balloon to create a seal of the balloon exterior surface relative to an inner wall of the appendage; and evacuating blood from a segregated interior space of the appendage distal of the balloon seal.

6. The method of claim 4 further comprising:

providing a secondary catheter having an elongated body with an outer diameter smaller than an inner diameter of the central lumen of the primary catheter;

inserting the secondary catheter into the central lumen of the primary catheter; and advancing the secondary catheter through the central lumen to the distal tip of the primary catheter.

7. The method of claim 4 further comprising:

providing a secondary catheter having a distal working portion for performing a treatment external to the primary catheter.

* * * * *